United States Patent [19]

Lauks

[11] Patent Number: 5,791,902
[45] Date of Patent: Aug. 11, 1998

[54] DRILL BIT FOR PRODUCING BONE CAVITIES FOR DENTAL IMPLANTS

[76] Inventor: Nikola Lauks, Saalkamp 8, D-22397 Hamburg, Germany

[21] Appl. No.: 724,074

[22] Filed: Sep. 30, 1996

[30] Foreign Application Priority Data

Sep. 30, 1995 [DE] Germany ............ 195 36 716.2

[51] Int. Cl.[6] ............................................. A61C 3/02
[52] U.S. Cl. ................................................. 433/165
[58] Field of Search .............................. 433/165, 166, 433/82; 408/57, 59; 606/80

[56] References Cited

U.S. PATENT DOCUMENTS

| | | | |
|---|---|---|---|
| 1,216,683 | 2/1917 | Greenfield | 433/165 |
| 4,511,334 | 4/1985 | Grafelmann | 433/165 |
| 4,820,156 | 4/1989 | Ross | 433/165 |
| 5,078,605 | 1/1992 | Sutter et al. | 433/165 |
| 5,098,293 | 3/1992 | Loof et al. | 433/165 |
| 5,261,818 | 11/1993 | Shaw | 433/165 |
| 5,435,722 | 7/1995 | Mandell | 433/165 |

FOREIGN PATENT DOCUMENTS 732213  6/1955  United Kingdom ............ 433/165

Primary Examiner—Cary E. O'Connor
Attorney, Agent, or Firm—Herbert Dubno

[57] ABSTRACT

A drill bit for producing bone cavities for dental implants having a shaft which is indexable in a dental drill handpiece and a cutting head for removal of the bone tissue. Between the shaft and the cutting head, a bit body is provided whose cross section has reduced dimensions by comparison with the bone cavity formed by the cutting head.

8 Claims, 2 Drawing Sheets

DRILL BIT FOR PRODUCING BONE CAVITIES FOR DENTAL IMPLANTS

FIELD OF THE INVENTION

My present invention relates to a drill bit for producing bone cavities for dental implants and, more particularly, to a drill bit of the type which has a cutting head adapted to remove bone material in the oral cavity to produce a cavity in the bone into which an implant can be anchored, and a shaft receivable in a drill, for example, the handpiece of a drilling tool, upon which the cutting head is carried.

BACKGROUND OF THE INVENTION

Drill bits for producing bone cavities on which a dental implant can be anchored in the jaw of a patient are known.

Generally the drill bit will have a bit body located between the cutting head and the shaft whose cross section is identical to that of the cutting head. The drawback of this type of drill bit is that the drill bit can jam in the previously drilled portion of the bone cavity as a result of pressure on the bone which tends to press the walls of the cavity against the body of the bit. This pressure on the bit body from the surrounding bone material can have a number of detrimental effects.

For example, it can increase the friction between the drill bit and the surrounding bone material and generate elevated friction heat which may be detrimental to the later healing of the implant in place and to the detriment of the reliability of the anchorage of the implant. The bone tissue can be traumatized by the excessive development of heat.

Further, because of the tendency of the bone material to grip the bit body between the head and the shaft, an undesired vibration can be set up during the drilling operation which limits the precision of the drilling operation and hence the cavity which is produced. The closeness of the walls of the previously drilled portion of the cavity to the bit body, moreover, can hinder the movement of the chips and other detritus of the drilling operation from the cavity, can impede the flushing of the cavity and can interfere with the drilling operation in this manner as well.

OBJECTS OF THE INVENTION

It is, therefore, the principal object of the present invention to provide an improved drill bit for the formation of bone cavities in the jaw of a patient for anchored dental implants therein whereby drawbacks of earlier drill bits are avoided.

Another object of the invention is to provide an improved drill bit for the purposes described which can form bone cavities with a highly increased precision by comparison with earlier drill bits and without traumatization of the bone tissue.

Still another object of this invention is to provide a drill bit for producing bone cavities for dental implants which represents a marked improvement over earlier drill bits.

SUMMARY OF THE INVENTION

These objects and others which will become apparent hereinafter are attained, in accordance with the invention, in that between the shaft and the cutting head, a bit body is provided whose cross section is of reduced dimensions by comparison with those of the cutting head and of the bone cavity formed thereby.

More particularly, a drill bit for producing bone cavities for receiving dental implants can comprise:

a shaft indexable in a drill to be driven thereby;

an elongated body secured to the shaft at one end of the body; and a cutting head secured to another end of the body opposite the shaft and dimensioned to drill a dental-implant cavity in bone of a patient, the body having a cross section of transverse dimensions less than corresponding dimensions of the drilled cavity.

Because of the resulting annular gap between the reduced cross section bit body and the remaining bone material, there is a reduction or complete elimination of friction between the bit body and the bone material and thus the bit body does not come into contact with the remaining bone structure at all. A vibration effect cannot arise. The bone material is not additionally heated by friction heat and thus there is substantially less frictional resistance to the drill bit which must be overcome by the drilling machine by comparison with earlier drill bits.

Furthermore, because of the annular gap between the drill body and the surrounding bone material, the removed bone material can be flushed more readily from the bone cavity and cooling by the Ringer solution used for the flushing operation is improved.

According to a feature of the invention, the head projects transversely beyond the transverse cross section of the body which can have a polygonal or round (circular) cross section. The body can have, adjacent the head, a bevel converging inwardly away from the head and forming a transition surface between the body and the head.

It has been found to be advantageous, moreover, to form the body with a succession of drilling-depth marking rings spaced apart along a length of the body.

According to a further feature of the invention, a flange is provided between the elongated body and the shaft and is dimensioned to be rotationally received in a drilling sleeve template for guiding the bit. The shaft, the flange and the body can be tranersed by a flushing passage having outlets or mouths formed in the body and at the head for discharging the flushing solution into the annular gap and the drilled portion of the cavity. The outlet formed at the head can be provided in a region of the head turned away from a cutting edge thereof.

The cutting head can be blade-shaped and can have a configuration and dimensions conforming substantially to a configuration and dimensions of an implant to be inserted into the cavity and I can provide a set of such drill bits with the heads being successively larger in size so that the cavity can be enlarged in a stepwise manner to the final dimensions for the particular implant.

BRIEF DESCRIPTION OF THE DRAWING

The above and other objects, features, and advantages will become more readily apparent from the following description, reference being made to the accompanying drawing in which.

SPECIFIC DESCRIPTION

As can be seen from FIGS. 1 through 6, a drill bit according to the invention includes a shaft 1 which can be indexed in the handpiece of a dental drill and carries a cutting head 2 capable of drilling into bone material as shown at 11 to produce a cavity 12 which has a configuration and dimension conforming to a dental implant to be received in the cavity.

Between the cutting head 2 and the shaft 1 is a bit body 3 whose cross section has reduced dimensions by comparison to that of the bone cavity drill bit cutting head 2. The cutting head 2 thus extends transversely beyond the bit body 3.

Figure 3:
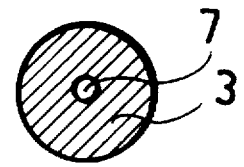
FIG. 3 is a cross sectional view along the line III—III thereof.
Figure 2:
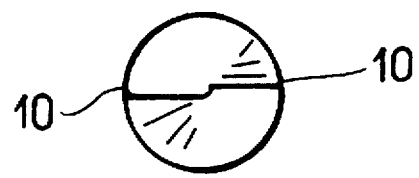
FIG. 2 is an end view of the cutting head of this drill bit.
Figure 4:
FIG. 4 is a cross sectional view of an alternative configuration of the body of the drill bit.
Figure 5:
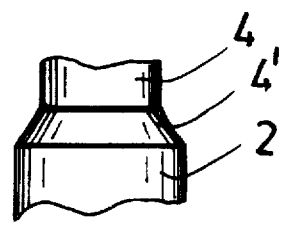
FIG. 5 is a fragmentary elevational view showing the transition surface between the cutting head and the bit body.

As can be seen from FIG. 4, the bit body 3' can be of polygonal, e.g. square, cross section although, as illustrated in FIG. 3, the cross section can be round, i.e. circular. The transition regions 4 between the body 3 and the cutting head 2 (compare FIG. 5) and, if desired, between the bit body 3 and the flange 6, may be beveled or chamfered as shown at 4' in FIG. 5.

The bit body 3 is provided with marking rings 5, e.g. of different coloration, which signal the depth of penetration of the bit in the bone tissue.

Figure 1:
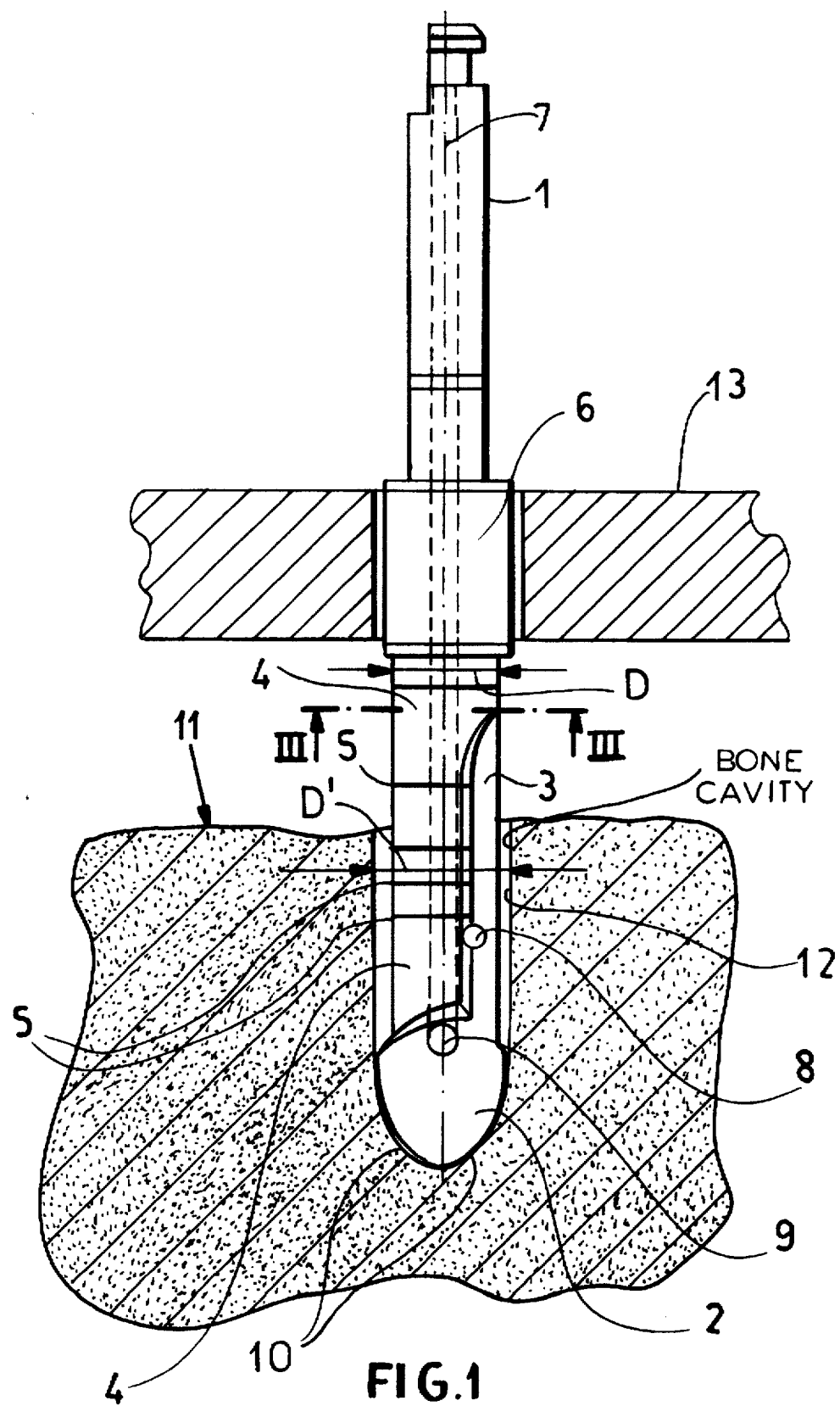
FIG. 1 is an elevational view of a drill bit for boring implant-receiving cavities in bone tissue, showing a template and the bone tissue in cross section.
Figure 6:
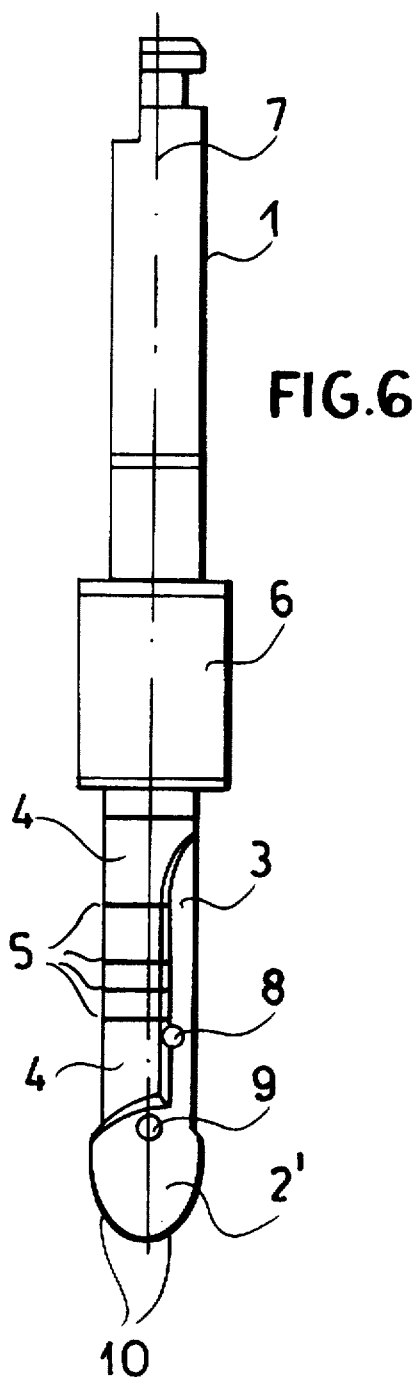
FIG. 6 is an elevational view of a drill bit which, together with the drill bit of FIG. 1 can form a set whereby the cavity produced in the bone tissue can be stepwise enlarged to the final dimensions.

The flange 6 provided between the bit body 3 and the shaft 1 can be dimensioned to allow rotatable journalling of the bit in the drill guide sleeve of a template 13 shown only diagrammatically in FIG. 1. A template as can be used with the drill bits of the invention is described, for example, in European Patent 0 328 911.

The shaft 1, the flange 6 and the bit body 3 are longitudinally traversed by a flushing passage 7 whose outlets 8 and 9 open laterally into the drilled cavity and are provided in the bit body 3 and in the vicinity of the cutting head 2 respectively. The outlet 9 in the vicinity of the cutting head 2 is preferably provided in a region of the cutting head turned away from a cutting edge or blade 10 of the cutting head. The cutting head 2 is preferably blade shaped so that it has a minimum of contact with the bone material apart from the cutting head. As has been noted, the shape and dimensions of the cutting head 2 preferably will correspond to the configuration and dimensions of the drilled cavity in the completed drilling operation. As a comparison of FIGS. 1 and 6 will show, a series or set of drill bits is provided with cutting heads 2 and 2' which are stepped in the sense that in the series of drill bits each cutting head is progressively larger to allow stepwise use of the drill bits to enlarge the bone cavity in stages to the final configuration after an initial pilot drill has formed a bore in the bone tissue. This stepwise enlargement of the bone cavity further minimizes traumatization of the bone tissue and all of the bits of the series have reduced cross section bit bodies so that jamming of the drill bit in the cavity formed by each can be avoided, the force with which the drill is applied can be minimized and the danger of an imprecise cavity is eliminated.

I claim:

1. A drill bit for producing bone cavities for receiving dental implants, said drill bit comprising:

a shaft indexable in a drill to be driven thereby;

an elongated body secured to said shaft at one end of said body;

a flange formed between said body and said shaft and dimensioned to be rotatably received in a drilling sleeve template for guiding the bit; and a rounded blade cutting head secured to another end of said body opposite said shaft and dimensioned to drill a dental-implant cavity in bone of a patient, said body having a cross section of transverse dimensions less than corresponding dimensions of the drilled cavity, said cutting head extending over a length of said drill bit which is substantially shorter than said body and projecting transversely beyond a transverse cross section of said body, said shaft, said flange and said body being traversed by a flushing passage having outlets formed in said body and at said head.

2. The drill bit defined in claim 1 wherein said body has a polygonal cross section.

3. The drill bit defined in claim 1 wherein said body has adjacent said head a bevel converging inwardly away from said head.

4. The drill bit defined in claim 1 wherein said body has a round cross section.

5. The drill bit defined in claim 1 wherein said body is provided with a succession of drilling-depth marking rings along a length of the body.

6. The drill bit defined in claim 1 wherein said outlet formed at said head is provided in a region of said head turned away from a cutting edge thereof.

7. The drill bit defined in claim 1 wherein said cutting head has a configuration and dimensions conforming substantially to a configuration and dimensions of an implant to be inserted in said cavity.

8. The drill bit defined in claim 1 which is part of a set of drill bits configured for successive use for stepwise enlargement of the cavity to ultimately accommodate a dental implant.

* * * * *